United States Patent
Zaykova-Feldman et al.

(10) Patent No.: US 7,446,542 B2
(45) Date of Patent: Nov. 4, 2008

(54) APPARATUS AND METHOD FOR AUTOMATED STRESS TESTING OF FLIP-CHIP PACKAGES

(75) Inventors: Lyudmila Zaykova-Feldman, Dallas, TX (US); Thomas M. Moore, Dallas, TX (US)

(73) Assignee: Omniprobe, Inc., Dallas, TX (US)

( * ) Notice: Subject to any disclaimer, the term of this patent is extended or adjusted under 35 U.S.C. 154(b) by 298 days.

(21) Appl. No.: 11/367,562

(22) Filed: Mar. 3, 2006

(65) Prior Publication Data

US 2006/0210140 A1 Sep. 21, 2006

Related U.S. Application Data

(60) Provisional application No. 60/658,913, filed on Mar. 4, 2005.

(51) Int. Cl.
*G01R 31/302* (2006.01)
*G01R 31/28* (2006.01)

(52) U.S. Cl. ..................... 324/750; 324/158.1

(58) Field of Classification Search .............. 324/158.1, 324/765, 760, 750–752; 73/12.01, 12.14, 73/587, 750; 702/193, 141, 190, 174, 184
See application file for complete search history.

(56) References Cited

U.S. PATENT DOCUMENTS

| | | | |
|---|---|---|---|
| 5,319,977 A * | 6/1994 | Quate et al. ................... 73/606 |
| 5,412,997 A | 5/1995 | Hu et al. | |
| 5,438,402 A | 8/1995 | Gupta | |
| 5,852,232 A | 12/1998 | Samsavar et al. | |
| 5,992,242 A | 11/1999 | Murphy et al. | |

(Continued)

FOREIGN PATENT DOCUMENTS

JP    H02-126255 A    1/1992

(Continued)

OTHER PUBLICATIONS

Wong, E.J., et al, Drop Impact: Fundamentals and Impact Characterisation of Solder Joints, Instron Corporation, Norwood, Massachusetts, USA, May 19, 2005.

(Continued)

*Primary Examiner*—Ha Nguyen
*Assistant Examiner*—Tung X Nguyen
(74) *Attorney, Agent, or Firm*—John A. Thomas (57) ABSTRACT

An apparatus for testing flip-chip packages has a programmed computer, a test-engine stage for applying an impact to at least one package under test, and a monitoring stage. The test-engine stage causes an impact on the package on the side opposite its ball-grid array. The test-engine stage has actuators connected to the test-engine stage and the computer, for moving and aligning the test-engine stage. The monitoring stage has a digital camera connected to the computer for transmitting digital images from the ball-grid array side of the package to the computer. A microscope is preferably connected to the digital camera. A sample stage located between the test-engine stage and the monitoring stage holds the package under test. The sample stage has an acoustic transducer capable of being removably connected to the package under test. The acoustic transducer is connected to the computer for transmitting signals from the acoustic transducer to the computer.

7 Claims, 9 Drawing Sheets

U.S. PATENT DOCUMENTS

| | | | |
|---|---|---|---|
| 6,877,365 B2 * | 4/2005 | Watanabe et al. | ............ 73/105 |
| 2004/0181304 A1 | 9/2004 | Collier | |
| 2004/0217767 A1 | 11/2004 | DiOrio et al. | |
| 2005/0026476 A1 | 2/2005 | Mok et al. | |
| 2006/0096385 A1 | 5/2006 | Wenski | |
| 2006/0097727 A1 | 5/2006 | Messenger et al. | |
| 2006/0104561 A1 | 5/2006 | Ivtsenkov | |
| 2006/0108896 A1 | 5/2006 | Nanataki et al. | |
| 2006/0108897 A1 | 5/2006 | Nanataki et al. | |

FOREIGN PATENT DOCUMENTS

| | | |
|---|---|---|
| JP | H05-0065450 A | 5/1994 |
| WO | WO 2004/083831 A1 | 9/2004 |

OTHER PUBLICATIONS

Teo, Mary et al, Correlation of Material Properties to Reliability Performance of Anisotropic Conductive Adhesive Flip Chip Packages, IEEE Transactions on Components and Pack.

Gupta, V., et al, Measurement of Solder Joint Strength and its Dependence on Thermal Aging in Freestanding and Board-Mounted Packages Using a Laser Spallation Technique, Confer.

Miller, M. R., Laser Spallation Adhesion Metrology for Electronic Packaging Development, Electronic Components and Technology Conference Proceedings from the 26th ISTFA, 2000.

Gupta, V., Measurement of Interfacial Adhesion and its Degradation in Multi-layer Packages, Devices, and Blanket Films using the Laser Spallation Technique, Conference Proceed.

Wong, E. H., et al, Tackling Drop Impact Realiability of Electronic Packaging, International Electronic Packaging Technical Conference and Exhibition (IPACK2003-35100), Maui, H.

Physics and Chemistry of Solids, Rain Erosion Apparatus [online]. Cavendish Laboratory, Madingley Road, Cambridge CB3 0HE, UK [retrieved on Mar. 04, 2006]. Retrieved from the I.

Wagner, L.C., Mechanical Testing in IC Packaging, Characteriztion of Integrated Circuit Packaging Materials, Moore, Thomas M., et al, eds., 1993, pp. 243-246, Butterworth-Hein.

Sharma, R, et al, Solder-Bumped Flip Chip Interconnect Technologies: Materials, Processes, Performance, and Reliability, Characterization of Integrated Curcuit Packaging Mate.

Newman, Keith, BGA Brittle Fracture—Alternative Solder Joint Integrity Test Methods, pp. 1194-1201, Proc. 55th Electronic Components and Technology Conference, May 31, 2005.

Wong, E.H., et al., "Drop Impact: Fundamentals and Impact Characterisation of Solder Joint," Instron Corporation, Norwood, Massachusetts, USA, May 19, 2005.

Teo, Mary, et al., "Correlation of Materials Properties to Reliability Performance of Anisotropic Conductive Adhesive Flip Chip Packages", IEEE Transactions on Components and Packaging Technologies, vol. 28, No. 1, Mar. 2005.

Gupta, V., et al., "Measurement of Solder Joint Strength and its Dependence on Thermal Aging in Freestanding and Board-Mounted Packages Using a Laser Spallation Technique", Conference Proceedings from the 30$^{th}$ ISTFA, 2004, pp. 267-276, ASM International, USA.

Miller, Mikel R., et al., "Laser Spallation Adhesion Metrology for Electronic Packaging Development", Electronic Components and Technology Conference Proceedings, 2002, The Printing House, USA.

Gupta, Vijay, et al, "Measurement of Interfacial Adhesion and its Degradation in Multi-layer Packages, Devices, and Blanket Films using the Laser Spallation Technique", Conference Proceedings from the 26$^{th}$ ISTFA, 2000, pp. 25-33, ASM International, USA.

Wong, E. H., et al., "Tackling Drop Impact Reliability of Electronic Packaging," International Electronic Packaging Technical Conference and Exhibition (IPACK2003-35101), Maui, Hawaii, USA, Jul. 6-11, 2003.

Physics and Chemistry of Solids, "Rain Erosion Apparatus" [online]. Cavendish Laboratory, Madingley Road, Cambridge CB3 0HE, UK. [retrieved on Mar. 04, 2006], Retrieved from the Internet: <URL: http://www-pcs.phy.cam.ac.uk/fsp/oldpage.html> (access "Rain Erosion" link).

Wagner, L.C., Mechanical Testing in IC Packaging, Characterization of Integrated Circuit Packaging Materials, Moore, Thomas M., et al, eds., 1993, pp. 243-246, Butterworth-Heinemann, Manning, USA.

Sharma, R., et al., Solder-Bumped Flip Chip Interconnect Technologies: Materials, Processes, Performance, and Reliability, Flip Chip Technologies, 1995, pp. 123-153, McGraw-Hill, USA.

International Searching Authority, International Application No. PCT/US06/007700, International Search Report and the Written Opinion, Feb. 20, 2007.

International Preliminary Examining Authority, Application No. PCT/US06/07700, International Preliminary Report on Patentability, Jul. 3, 2007.

* cited by examiner

APPARATUS AND METHOD FOR AUTOMATED STRESS TESTING OF FLIP-CHIP PACKAGES

CLAIM FOR PRIORITY

This application claims the priority of U.S. Provisional Patent Application Ser. No. 60/658,913, filed Mar. 4, 2005, which provisional application is incorporated into the present application by reference.

BACKGROUND

Flip-chip technology is defined as mounting the chip on a substrate using a variety of interconnect materials and methods as long as the chip surface, i.e. the active circuit, is facing the substrate. In this technique, solder bumps are attached to the input-output pads of the die at the wafer level. The flip-chip technique is the high-performance alternative to wire bonding techniques. Flip chips are cost effective and allow the realization of very slim and compact products, with increased I/O density and system miniaturization.

The most well-known and successful flip-chip technology today, IBM's solder-bumped flip-chip technology, evolved into the ball-grid array (BGA) packaging of integrated circuits. BGA packaging is scaling into smaller solder ball pitches and smaller individual solder ball sizes. Due to this smaller size, the requirements on packaging reliability, including the solder joint reliability, are becoming stricter. There are several different testing techniques of solder joint reliability in use in the industry, concentrating mostly on thermal performance.

There is a need for a mechanical stress testing technique, preferably using a relatively simple and inexpensive instrument. The ideal test environment would be the one very close to the application environment, with the possibility to produce an impact on the flip-chip package in a controllable way. The proposed method and apparatus of flip-chip test environment describes a testing process including different types of impact vehicles.

DESCRIPTION

The preferred embodiment includes a novel method and apparatus for mechanical flip-chip die and BGA package testing environment. In the preferred embodiment, the testing system comprises of three major components, computer for process control and an optional pick-and-place robot for replacement of sample packages. These three major components are: the sample stage, the test engine stage and the monitoring stage.

The Sample Stage

Figure 1:
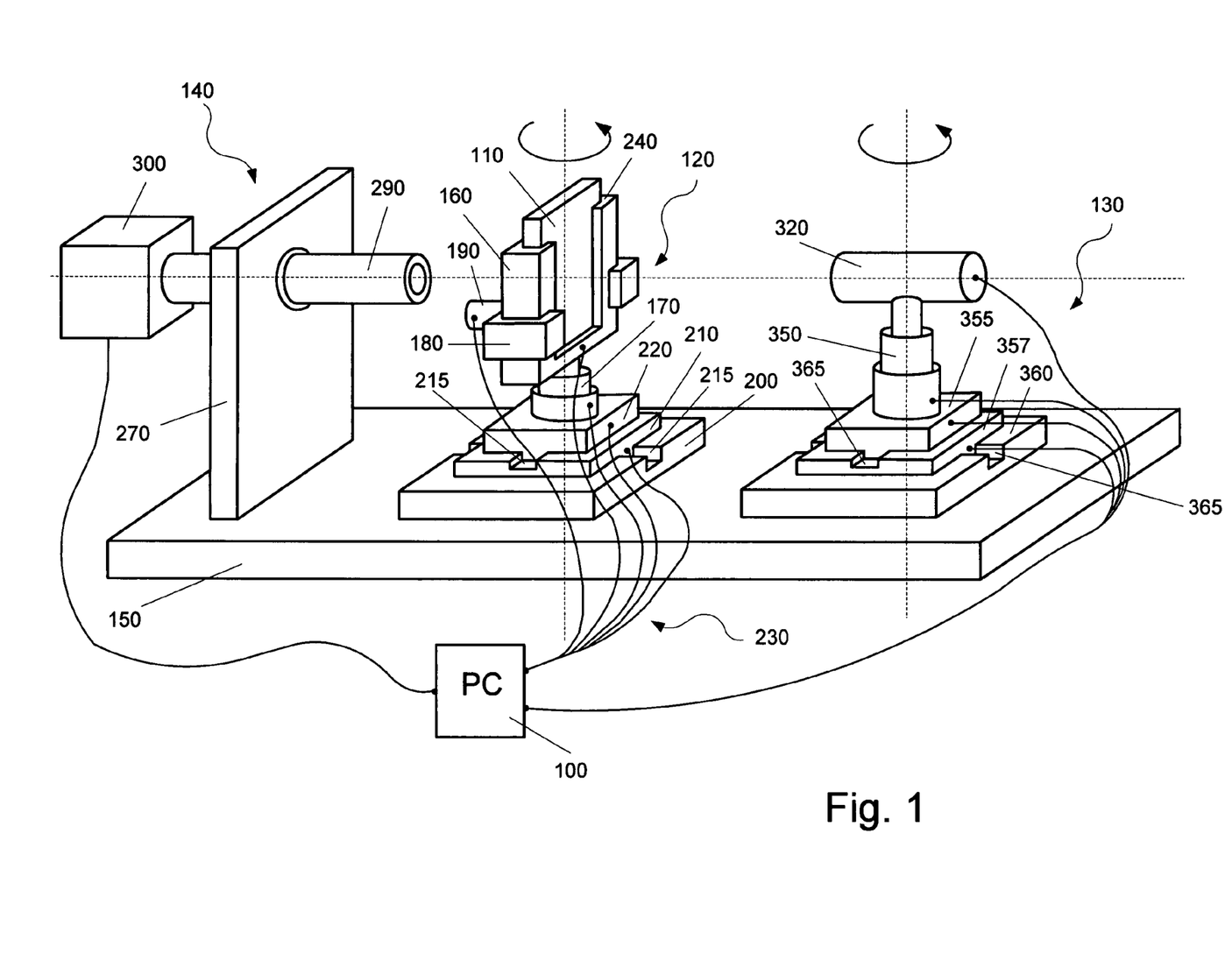
FIG. 1 is a perspective view of a mechanical stress testing system.

In the preferred embodiment, the sample stage (120) comprises a base (160) where the sample package (110) is inserted, the telescopic stand (170) holding the base (160), the frame (180) holding the acoustic transducer (190), and two small platforms (200) and (210) for horizontal movement in two perpendicular directions.

The lower small platform (200) is rigidly attached to a base platform (150), where all three stages are located. Both lower (200) and middle (210) small platforms comprise two tracks (215) intended for the movement of each small platform in one of the perpendicular horizontal directions.

The base (160) holding the package (110) is set on a telescopic stand (170). The telescopic stand (170) is rigidly attached to an upper small platform (220) and enables the vertical movement of a base (160) and turning it around its axis coincidentally with the telescopic stand (170) axis.

The outer frame (180) holding the acoustic transducer (190) is attached to a package base (160) with the possibility to change its position relative to the base vertical stands. The acoustic transducer (190) is mounted in an opening in the frame (180). The inner end of the acoustic transducer (190) is directly connected to a package (110), and an acoustic gel is applied to a place where the contact between the package (110) and the acoustic transducer (190) is made, to ensure good acoustic contact. Suitable acoustic transducers are manufactured by Panametrics, Inc. The position of a frame holding the acoustic transducer (190) can be manually or automatically adjusted to make contact between the sample package (110) and the acoustic transducer (190) in a place which will assure the best performance of the acoustic transducer (190).

As shown in FIG. 1, the small platforms (200), (210) and (220), the telescopic stand (170) and the acoustic transducer (190) are connected by appropriate electrical wiring (230) to a controlling computer (100) to ensure their proper movement and the feedback control. These wires (230) can be extended either outside or inside the stage (120). Motion control and feedback control can be accomplished by means known in the art, using actuators, position encoders and controlling software such LabVIEW supplied by National Instruments, Inc., of Austin, Tex.

The base (160) holding the package (110) has vertical rails (240) where the package (110) is inserted and is held for the test. These vertical rails (240) have several clamps (not shown) located at an appropriate distance for each package size. There is a possibility to insert several packages (110) vertically and conduct the stress test for several packages (110) in one testing session. The packages (110) can be brought to a testing site in a standard JEDEC tray and can be picked up and inserted into a base manually. Alternatively, a conventional autoloader can be used to insert the special JEDEC standard tray into a holder.

The Monitoring Stage

The monitoring stage (260) comprises the stand (270) with an opening (280) for holding the optical microscope (290), and a digital camera (300) attached to the optical microscope (290). The optical microscope (290) is used for alignment of the test engine (320) axis and the target area on the package (110) and for the detailed monitoring of the solder ball (330) displacement. The digital camera (300) is used for the recording of a stress test procedure and detailed solder ball (330) displacement. The digital camera (300) operation and the optical microscope (290) focus adjustment are electronically controlled by computer (100) using motion-control devices discussed above. All the details of the mechanical stress test procedure shown by the digital camera (300) can be displayed on a computer monitor screen. Only one of the digital camera (300) or optical microscope (290) need be moved.

The Test Engine Stage

The test engine stage (340) comprises the telescopic stand (350) holding the mounting for a test engine (340) and three small platforms (355, 357 and 360) for horizontal movement in two perpendicular directions. The lower small platform (360) is rigidly attached to a base platform (150), where all three major stages are located. The lower (360) and the middle (357) small platforms include two tracks (365) each for the movement in one of the perpendicular horizontal directions. The engine (320) for the package mechanical stress testing can be mounted on a telescopic stand (350) on the upper small platform (355), and as discussed below, can be any of several alternative devices. The mounting of a test engine (320) on a telescopic stand (350) gives the testing system the possibility of easy and fast test engine (320) replacement.

The Mechanical Stress Testing Method

Figure 2:
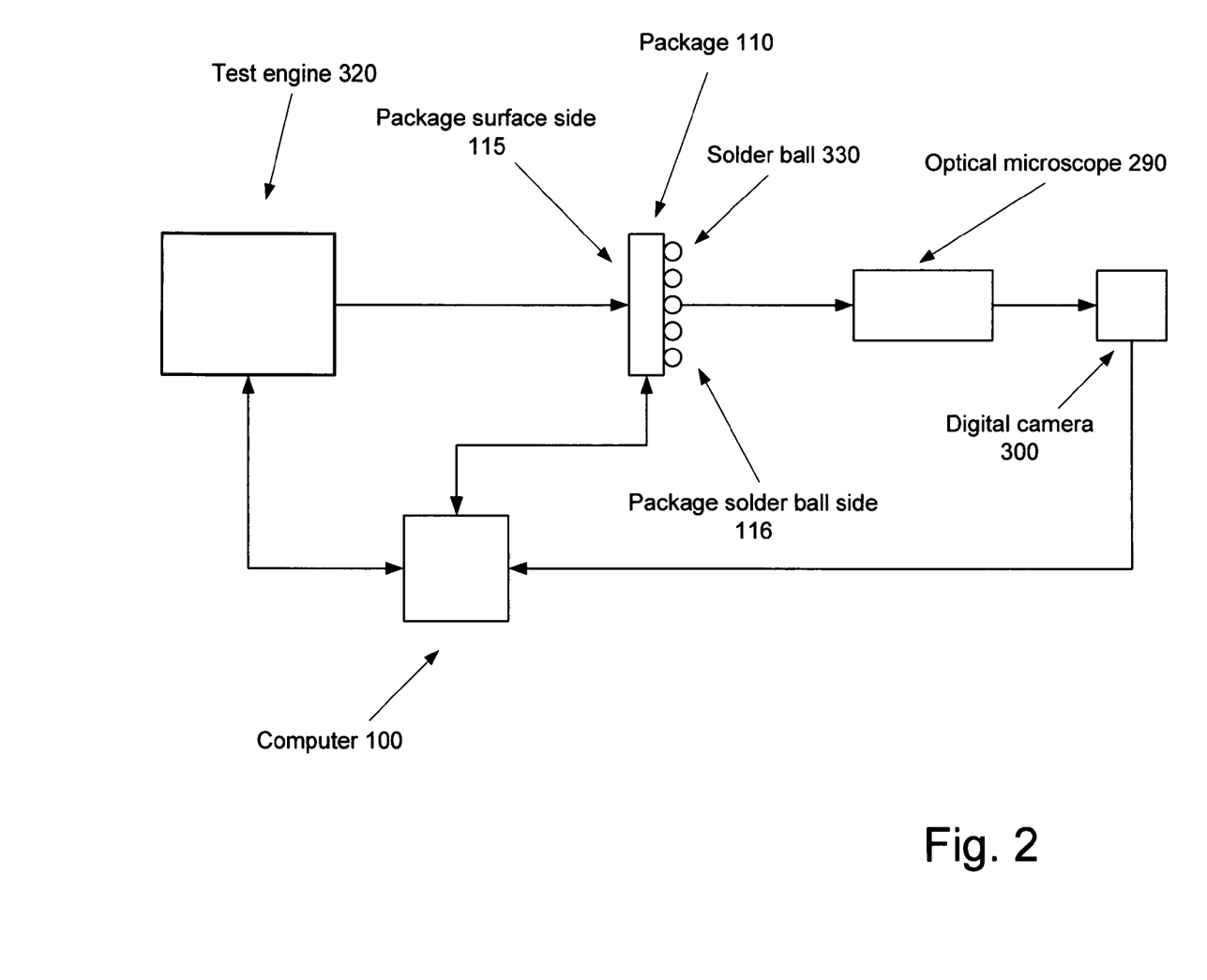
FIG. 2 is a schematic diagram of a mechanical stress testing system.
Figure 3:
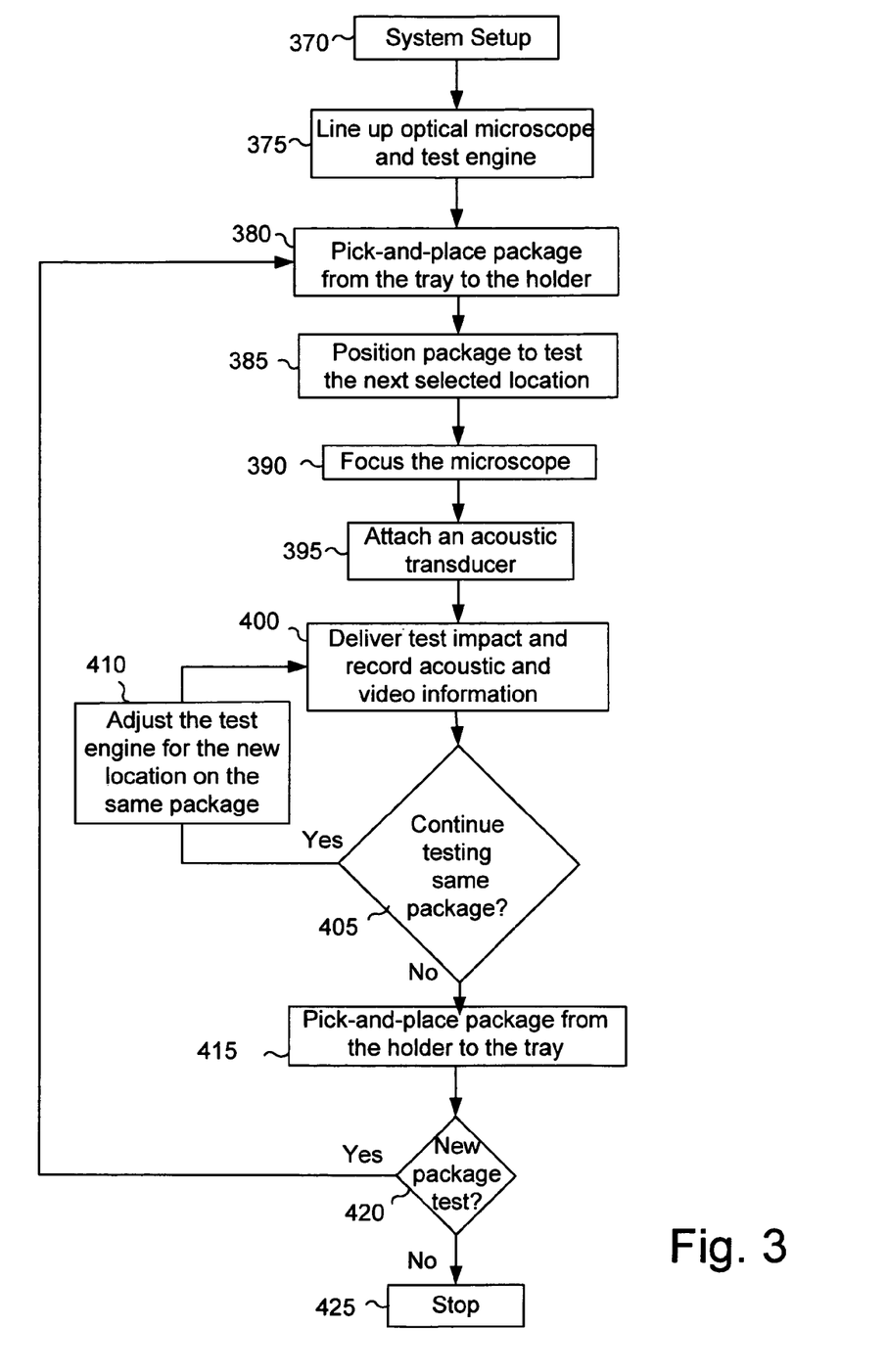
FIG. 3 is a flowchart of a mechanical automated stress testing process.
Figure 4:
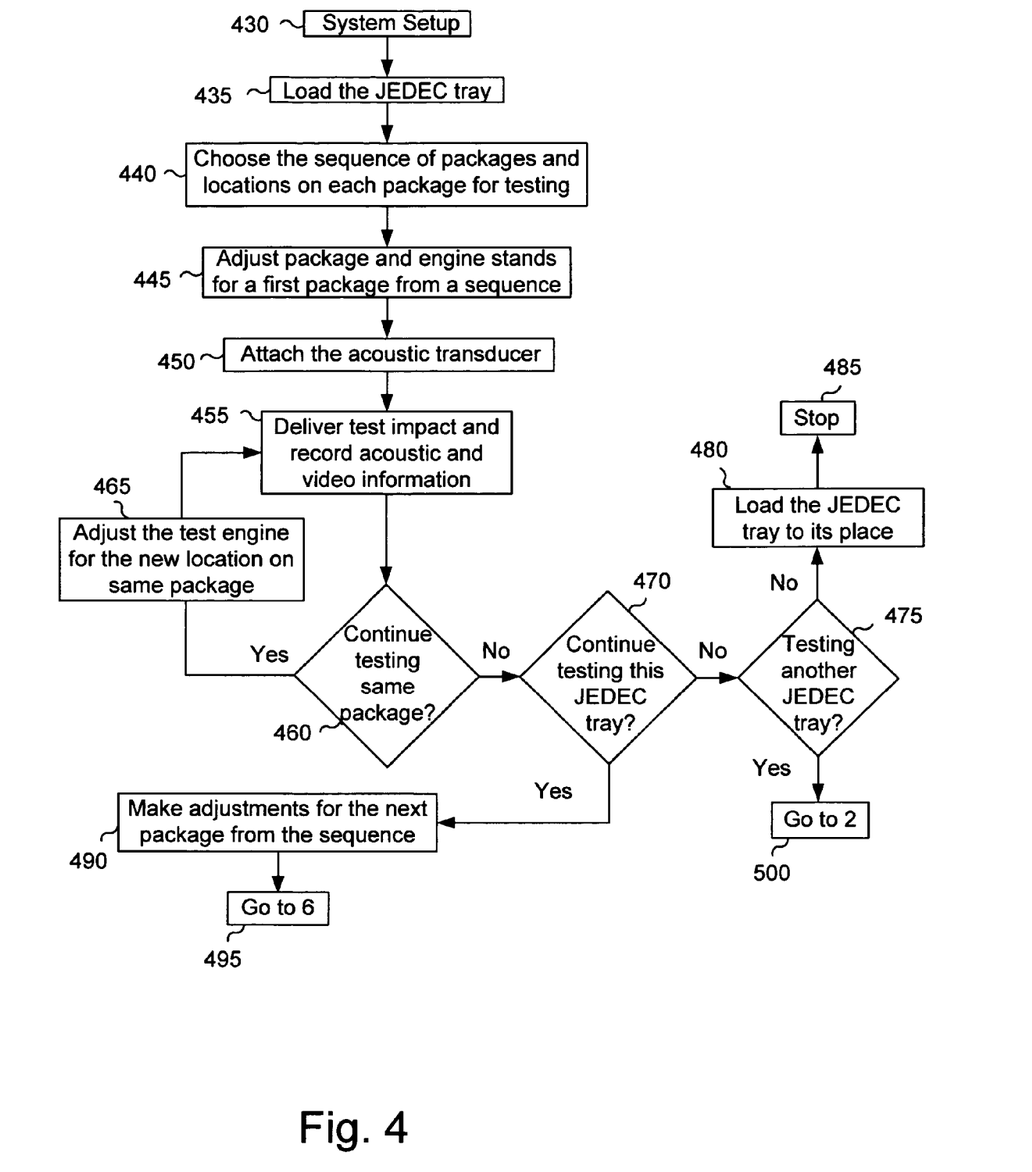
FIG. 4 is a flowchart of an alternative mechanical automated stress testing process.
Figure 5:
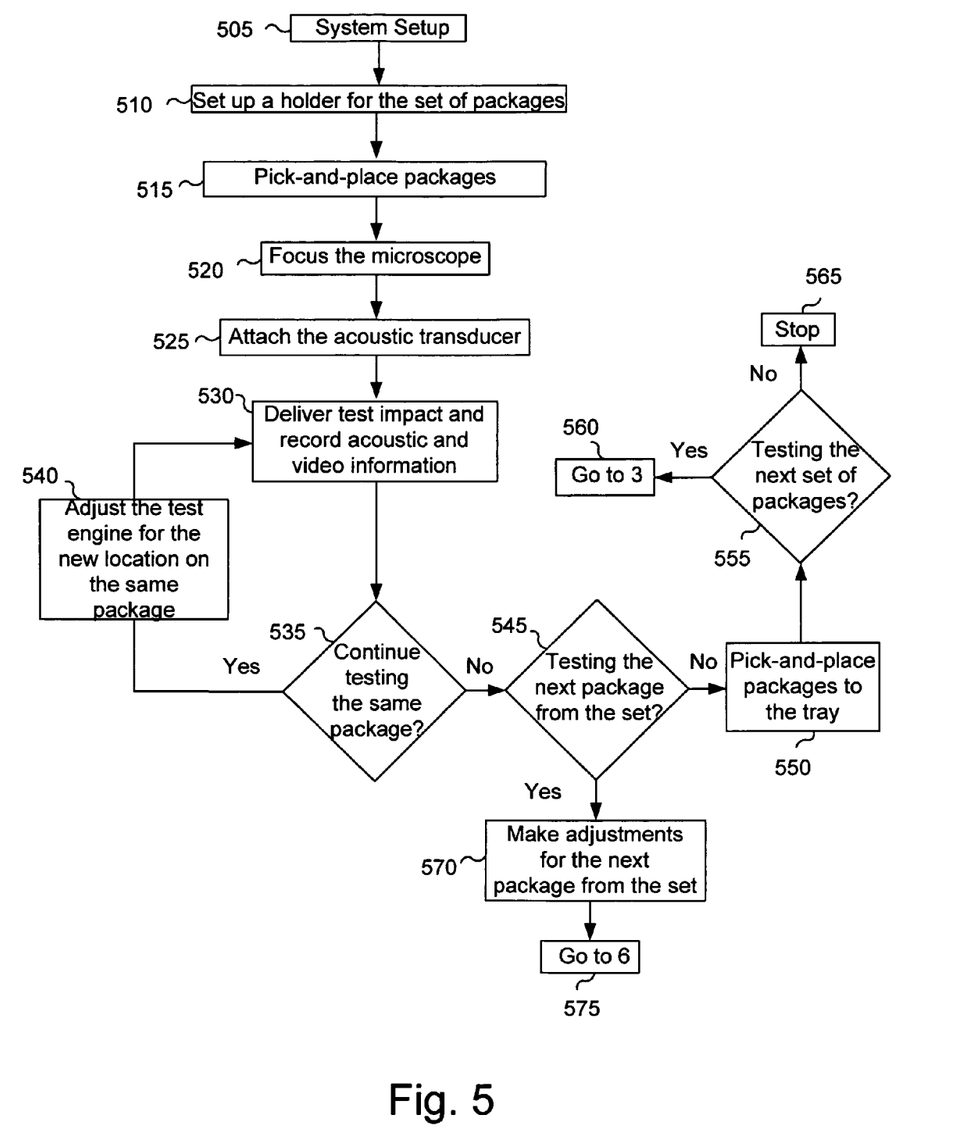
FIG. 5 is a flowchart of an alternative mechanical automated stress testing process.

The package (110) can be mechanically stress tested using the scheme shown in FIG. 2 and the flowcharts shown in FIGS. 3-5. Every package (110) can be picked from the special package tray and placed into a base holder (160) either manually or using a pick-and-place robot. Alternatively, a JEDEC standard tray can be used. The stress test engine (320) can be chosen from the set described in a Test Engine Stage section. Before placing the package (110) in the stand (160), the stress test engine (320) axis can be aligned with the optical microscope (290).

One or more packages (110) can be placed in a holder stand (160) in a fixed position. The packages (110) are positioned in a holder base (160) the way that the substrate side (115) faces the optical microscope (290). The optical microscope (290) is focused on a solder ball side (116) of the sample package (110). The multi-platform design of the stress test engine (320) and the sample stage setting (120) allows the fine adjustment of the test engine (320) and the package (110) positions. The package (110) receives an impact from the test engine (320) on the side opposite the side with the solder balls, possibly followed by the displacement of the solder ball (330) directly opposite the point of impact. The solder ball can be even separated from the package, depending on the intensity of the strike and the mechanical strength of the solder ball attachment. This event can be watched on a computer (100) monitor screen and recorded using the optical microscope (290) and the digital camera (300). This method allows the real-time operation and the adjustment of the impact strength to reach the desired result, from a small solder ball (330) displacement up to a crack in the package (110) substrate. The quantitative impact monitoring is being provided by the acoustic transducer (190) attached to a package (110) preferably on the solder ball side (380), but alternatively on the opposite side, on which the test impact is delivered. The accurate measurement of the velocity can be performed using two optical detectors (not shown) in the projectile path. The velocity and the known mass of the projectile can be used to quantify the test procedure. The mechanical shockwaves originated as a result of the impact can be transformed into an electric current using the acoustic transducer (190), with the signal sent to a computer (100).

The calibration of the test impact can be performed by detection of the magnitude of the acoustic signal or the characteristic acoustic signature of the impact event using a suitable signal-processing computer program. If using a pick-and-place robot, the entire process can be automated. The automated process flowcharts are shown in FIGS. 3-5. The case of one package is (110) shown in FIG. 3. In the scope of proposed method, there is a possibility to test as many locations on a the surface of a package (110) as needed. The case of testing the set of packages (110) is shown in FIG. 4. During the course of this procedure, the next package (110) is moved to a preferred testing position and tested, until the testing session is finished. Then the robot or an operator can replace the package (110) or a set of packages (110), and the process can be started over again. The case of a JEDEC tray testing is shown in FIG. 5.

In the preferred embodiment, a pneumatic projectile device is used as a test engine (320). This device allows impacting any desired location on a package (110) by adjusting its position using the telescopic stand and the small platforms' movement. The projectiles for this pneumatic device can be solid, or liquid droplets, or of any other appropriate material. The projectiles should be of a known mass and a uniform shape for quantitative and repeatable testing.

Figure 6:
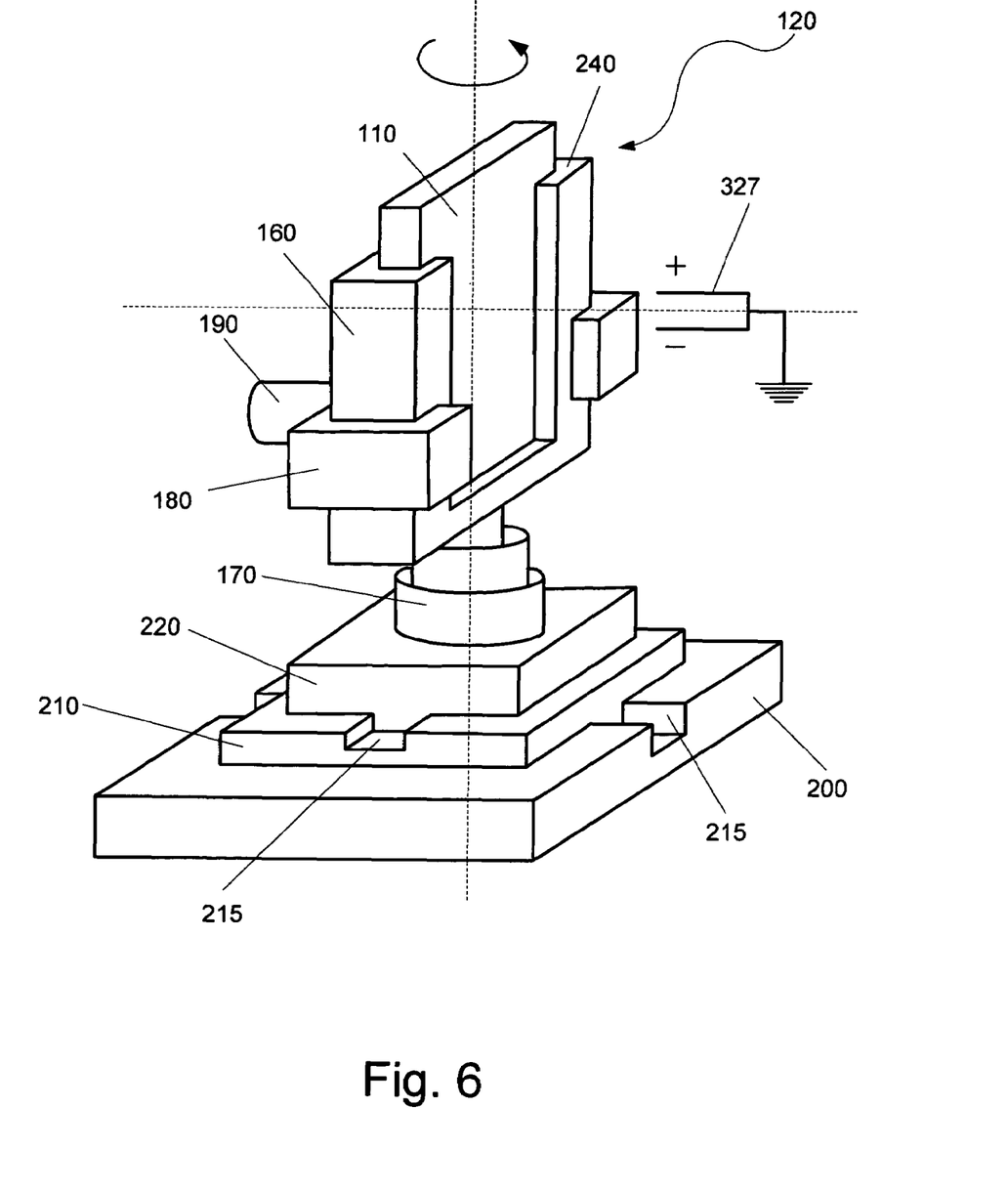
FIGS. 6-9 show alternate embodiments of the test engine.

In alternative embodiment, shown in FIG. 6, an electrical discharge source (327) can be used for flip-chip device stress testing. Such a capacitive discharge device, for example, can deliver an electric pulse to a target position on the device surface and generate the desired shock wave for testing.

Figure 7:
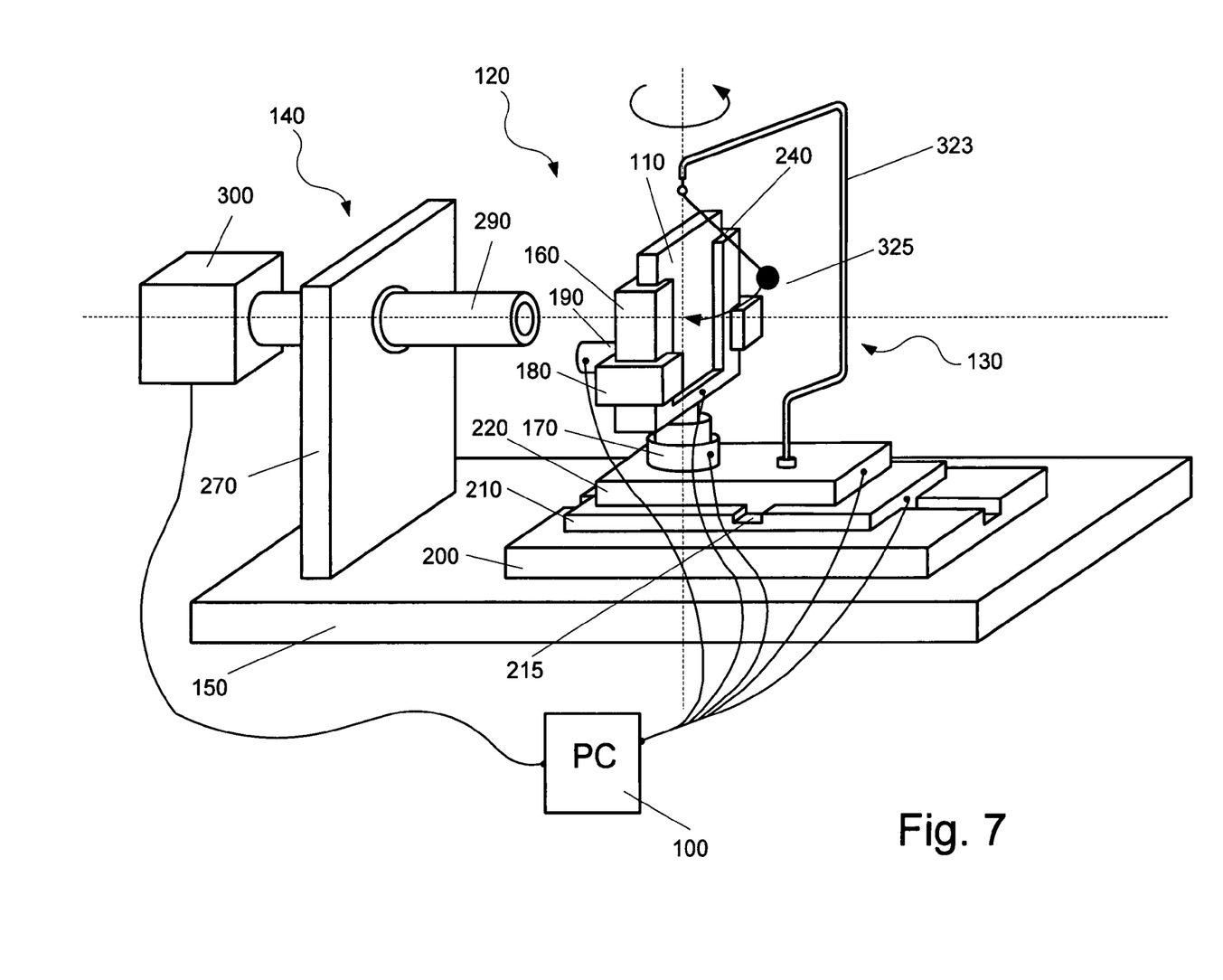

In another alternative embodiment shown in FIG. 7, a small pendulum (325) of known mass and released from a fixed height can be used for testing. The pendulum holder (323) can be positioned at an appropriate distance from the surface of the package (110), which is opposite the solder balls. The impact strength can be determined from the mass of the pendulum (325), the length of the pendulum arm and the release height. The position of an impact on a package surface can be adjusted via changing the position of the package (110).

Figure 8:
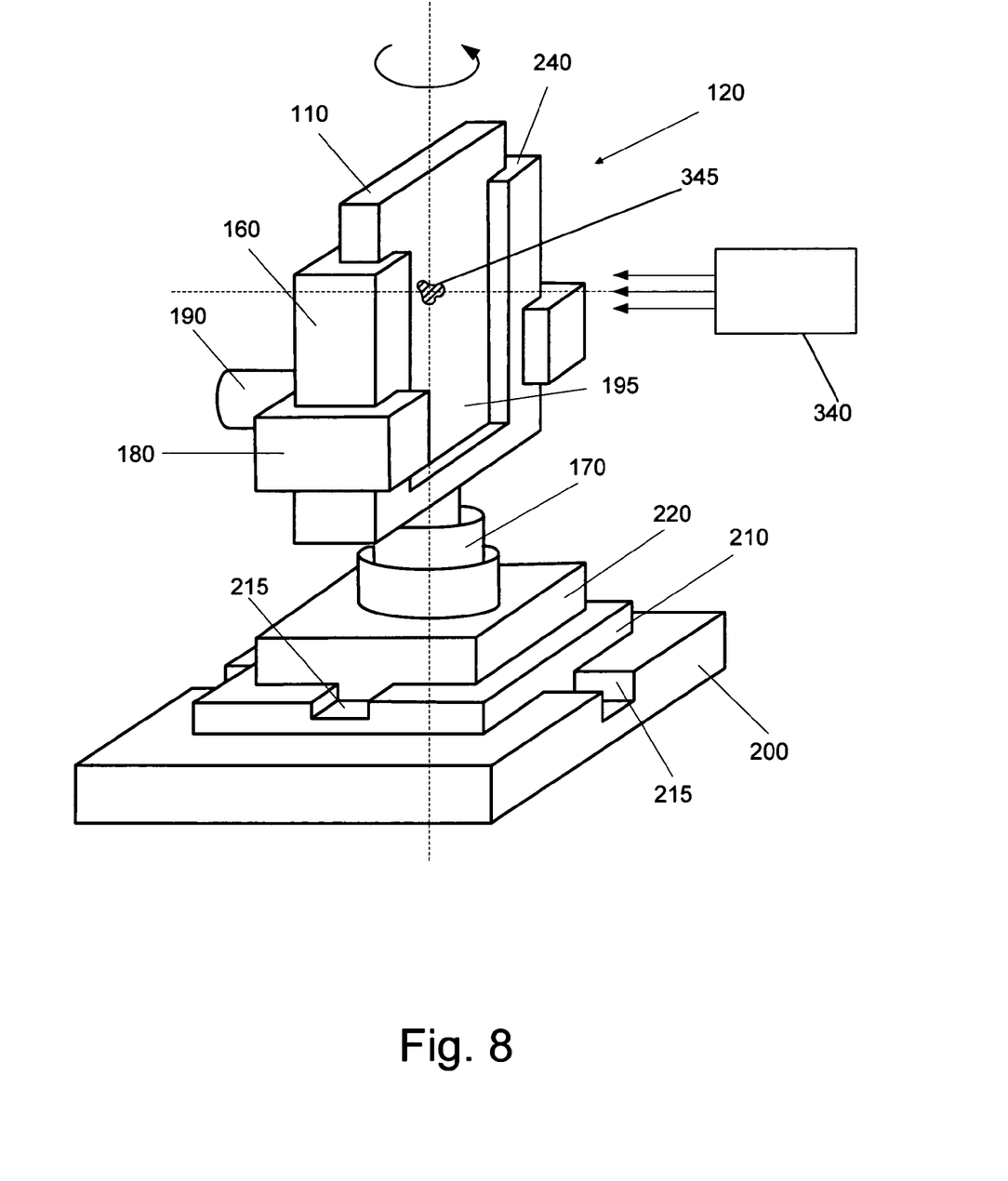

In another alternative embodiment shown in FIG. 8, small chemical or pyrotechnic explosives (345) with predetermined strength can be applied to a flip-chip package surface. For example, tiny drops of explosive material (345) can be deposited and dried at appropriate locations on the surface of the package (110), opposite the solder balls (330). Each of these dried droplets can then be detonated by an energy source (340) such as a laser beam, electric shock or localized heat source.

Figure 9:
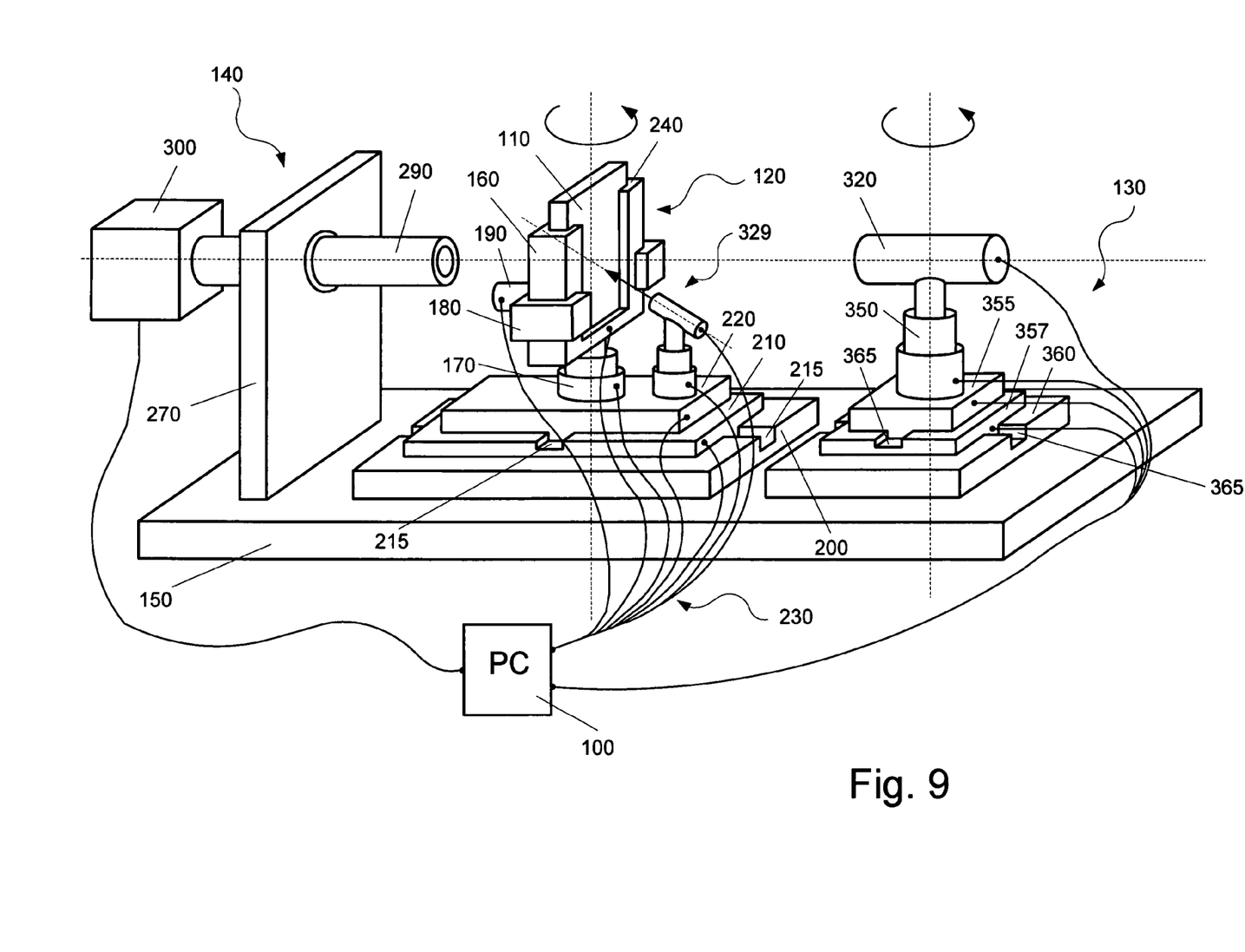

In another alternative embodiment shown in FIG. 9, a microwave radiation source (329) can be applied to either surface of the package (110) to produce a rapid thermal expansion within the package (110). Then a mechanical shockwave is applied as previously discussed to test the solder ball attachment under conditions of elevated temperature.

Since those skilled in the art can modify the specific embodiments described above, we intend that the claims be interpreted to cover such modifications and equivalents.

We claim:

1. An apparatus for testing flip-chip packages, comprising:
   a programmed computer;
   a test-engine stage for applying an impact to at least one package under test; the test-engine stage connected to the computer; the test-engine stage further comprising:
   actuators connected to the test-engine stage and the computer, for moving and aligning the test-engine stage
   a monitoring stage; the monitoring stage comprising:

a digital camera;
the digital camera connected to the computer for transmitting digital images to the computer;
a sample stage for holding a package under test; the sample stage located between the test-engine stage and the monitoring stage; where the sample stage further comprises:
an acoustic transducer; the acoustic transducer capable of being removably connected to the package under test;
the acoustic transducer connected to the computer for transmitting signals from the acoustic transducer to the computer.

2. The apparatus of claim 1 further comprising a microscope; the microscope connected to the digital camera.

3. The apparatus of claim 1 where the test-engine stage further comprises:
a pneumatic means for propelling a projectile to strike the package under test.

4. The apparatus of claim 1 where the test-engine stage further comprises:
a pendulum;
the pendulum disposed to strike the package under test when the pendulum is raised and dropped.

5. The apparatus of claim 1 where the test-engine stage further comprises:
a capacitor for storing an electric charge;
the discharge of the capacitor disposed to impart an impact to the package under test.

6. The apparatus of claim 1 where the test-engine stage further comprises:
an explosive disposed on the surface of the package under test.

7. The apparatus of claim 1 further comprising:
a source of microwave radiation for heating the package under test prior to imparting an impact to it.

* * * * *